United States Patent [19]
Hess et al.

[11] Patent Number: 4,800,898
[45] Date of Patent: Jan. 31, 1989

[54] NEURAL STIMULATOR ELECTRODE ELEMENT AND LEAD

[75] Inventors: Stanley R. Hess, Miami; Sandra L. Miller, N. Miami; Peter J. Pohndorf, Miami Shores; Peter P. Tarjan, Miami, all of Fla.

[73] Assignee: Cordis Corporation, Miami, Fla.

[21] Appl. No.: 30,281

[22] Filed: Mar. 26, 1987

Related U.S. Application Data

[63] Continuation of Ser. No. 540,123, Oct. 7, 1983, abandoned.

[51] Int. Cl.$^4$ .............................................. A61N 1/05
[52] U.S. Cl. .................................... 128/785; 128/786
[58] Field of Search .............................. 128/784–786, 128/419 P, 642

[56] References Cited

U.S. PATENT DOCUMENTS

| | | | |
|---|---|---|---|
| 3,664,347 | 5/1972 | Harmjanz | 128/786 |
| 3,939,843 | 2/1976 | Smyth | 128/419 P |
| 4,285,347 | 8/1981 | Hess | 128/785 |
| 4,301,815 | 11/1981 | Doring | 128/785 |
| 4,402,328 | 9/1983 | Dorning | 128/785 |
| 4,414,986 | 11/1983 | Dickhudt et al. | 128/785 |
| 4,430,999 | 2/1984 | Brigton et al. | 128/785 X |
| 4,432,377 | 2/1984 | Dickhudt | 128/419 P |
| 4,467,817 | 8/1984 | Harris | 128/786 |
| 4,549,556 | 10/1985 | Tarjan et al. | 128/785 |

*Primary Examiner*—Lee S. Cohen
*Attorney, Agent, or Firm*—Lockwood, Alex, FitzGibbon & Cummings

[57] ABSTRACT

A neural stimulator electrode element and lead includes an elongate sheath having a passage therein and which contains an electrical conductor and electrode, the latter of which communicates through the exterior wall of the sheath. Two pairs of flexible elongate wing members are positioned on the exterior wall of the sheath to stabilize the tip when it is installed in the patient's epidural space. The flexible wing members flex during installation, but extend laterally from the sheath following installation of the element to prevent the element and lead from rotating and maintain the element in position.

20 Claims, 1 Drawing Sheet

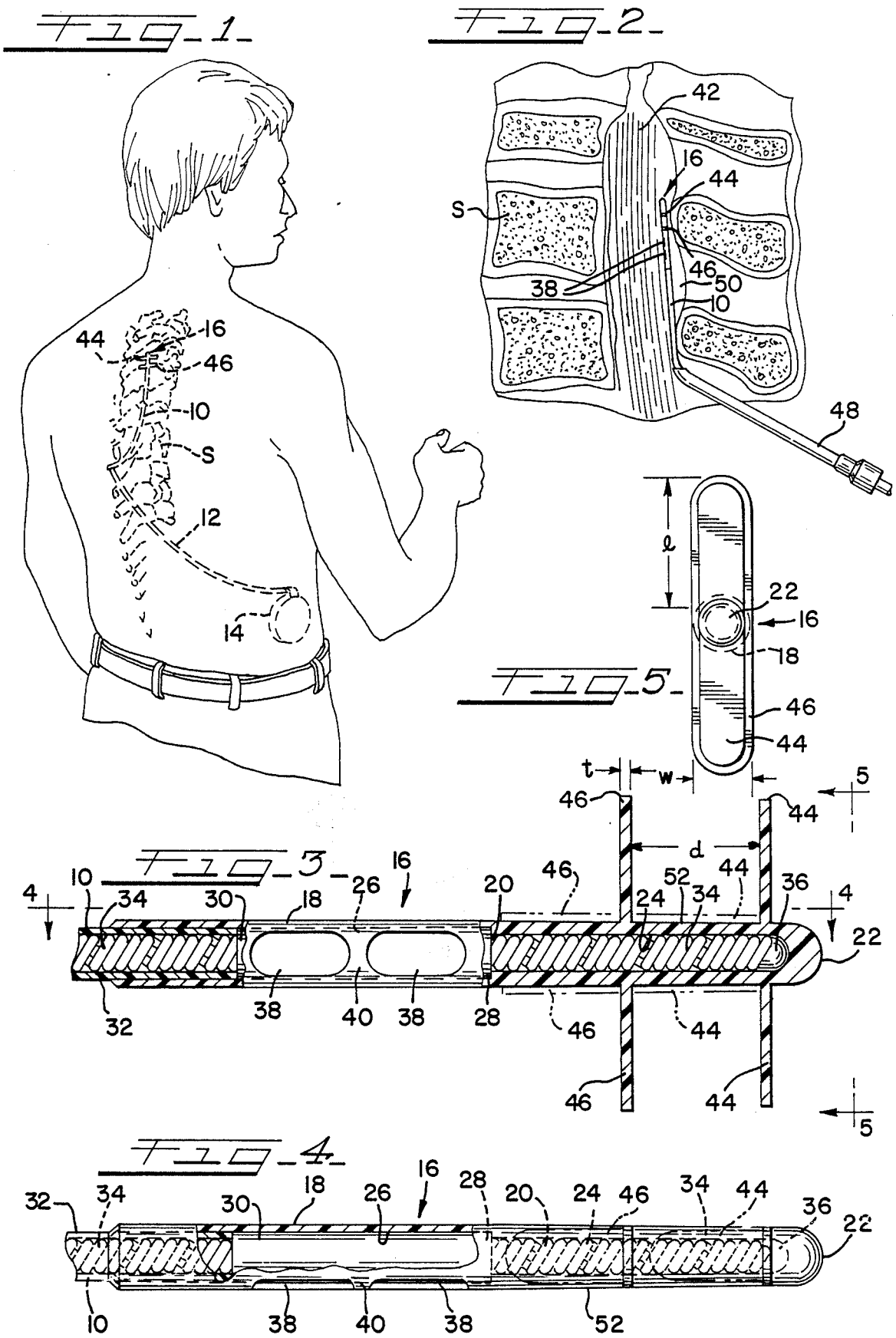

NEURAL STIMULATOR ELECTRODE ELEMENT AND LEAD

This application is a continuation of application Ser. No. 540,123, filed Oct. 7, 1983, now abandoned.

BACKGROUND AND SUMMARY OF THE INVENTION

The present invention relates to an electrode element and, in particular, to a neural stimulator element and lead for installation in a patient's epidural space to stimulate the patient's dura.

Neural stimulator electrodes and leads have been employed in the past which are installed in the epidural space of the spinal cord of a patient for stimulating selected locations along the spinal cord for such purposes as the relief of pain. As disclosed in U.S. Pat. No. 4,285,347 (Hess), it is generally advantageous to selectively direct the electrical current from such electrode directly against the dura in the spinal cord, rather than conduct the current omnidirectionally from the electrode. Selective direction of the current substantially reduces the power requirements and, thereby, substantially extends the life of the power generating source. This is advantageous particularly where the power generating source is subcutaneously implanted. Selective direction of the current and reduction of the current also reduces the possibility of side effects which might result from stimulation of undesired or unnecessary tissue.

It is important that the electrode and lead be stabilized after installation and fixation in the epidural space to prevent shifting of the electrode. It is also important to prevent rotation of the electrode particularly where the electrode is directional. Such shifting or rotation may occur, for example, during strenuous activity or exercise by the patient. If the electrode becomes rotated away from the dura at the site of stimulation, its desired effect will be greatly diminished and may be lost altogether. Moreover, other bodily tissue which need not be stimulated may instead be stimulated resulting in possible undesirable side effects.

In the aforementioned U.S. Pat. No. 4,285,347, an epidural lead stabilizing construction is disclosed which comprises three curved loops at the distal end of the lead which extend in three dimensions to effect the sought after stabilization. Although the stabilization produced by this curved loop construction may be satisfactory in many lead installations, it does have at least one disadvantage. Due to the presence of the three curved loops, a total of three stable rotational positions are possible. One of these positions is the desired position in which the electrode and two of the loops are in generally coplanar relationship to each other and lie against the dura to stabilize the directional electrode directly against the dura. The other two positions are caused by tilting of the third loop if it bears against a vertebra. When the third loop tilts one way or the other from being perpendicular to the dura, one of the remaining loops will bear against the dura, but the other loop and the electrode will also tilt so as to be angled away from the dura. These latter two positions are not desired because the directional electrode will be rotated out of direct contact with the patient's dura.

Neural stimulator elements and leads incorporating the principles of the present invention overcome these several aforementioned disadvantages. In an electrode element or lead of the present invention, a stylet need not be relied upon to retract or otherwise directly operate the stabilizers of the present invention. The stabilizers of the present invention are quite flexible in a direction parallel to the axis of the element. Thereby, the stabilizers readily flex into an inactive reclined position as they are passed through the implantation needle, such as a Tuohy needle, and through the epidural space of the patient. However, once the element has been located at its desired location at the dura, slight movement of the element in its reverse direction will readily cause the stabilizers to assume their stabilizing position and, in this position, will prevent shifting and rotation of the lead and electrode element. In a neural stimulator electrode element and lead of the present invention, the number of possible stable rotational positions is reduced to only two, only one of which is undesirable, thereby facilitating placement and stabilization of the electrode against the dura.

In one principal aspect of the present invention, an electrode element for a neural stimulator lead includes an elongate sheath and a passage in the sheath extending axially thereof which is adapted to receive an electrical conductor. The electrode is positioned in the passage and communicates through the exterior wall of the sheath. A pair of flexible elongate members on the exterior wall of the sheath extend laterally from the sheath at a substantial angle to the axis of the elongate sheath. Each of the members is attached at one end to the exterior wall of the sheath and the other end is free. The flexible members are capable of flexing adjacent their attached end so as to move between their laterally extending position to a position adjacent the exterior wall of the sheath and substantially parallel to the axis of the sheath.

In another principal aspect of the present invention, each of the aforementioned flexible members has a width which is substantially greater than its thickness and the width extends substantially perpendicular to the axis of the sheath.

In still another principal aspect of the present invention, when the aforementioned flexible members are in their laterally extending position, they extend substantially perpendicular to the axis of the sheath.

In still another principal aspect of the present invention, the aforementioned electrode communicates through a portion only of the perimeter of the exterior wall of the sheath and the flexible members are attached to the exterior wall of the sheath at approximately 90° from the portion through which the electrode communicates.

In still another principal aspect of the present invention, the perimeter of the aforementioned sheath is smaller adjacent the flexible members than it is in the remainder of the sheath.

In still another principal aspect of the present invention, the aforementioned flexible members are between the distal end of the sheath and the electrode.

In still another principal aspect of the present invention, in the aforementioned electrode elements at least one opening extends through the exterior wall of the sheath at the electrode for communicating the electrode with the exterior wall.

In still another principal aspect of the present invention, coupling means is included in the aforementioned electrode elements adjacent the end of the sheath for coupling the element to the neural stimulator conductor and the conductor is combined therewith.

In still another principal aspect of the present invention, two pairs of the aforementioned flexible members are provided, each of the pairs being spaced from each other along the axis of the sheath by a distance greater than the length of each flexible member.

In still another principal aspect of the present invention, the aforementioned electrode elements are the tip for the neural stimulator lead.

These and other objects, features and advantages of the present invention will be clearly understood through a consideration of the following detailed description.

BRIEF DESCRIPTION OF THE DRAWING

In the course of this description, reference will frequently be made to the attached drawing in which:

FIG. 1 is an overall perspective view of a patient in which a neural stimulator lead and electrode element comprising a lead tip have been installed and stabilized in accordance with the principles of the present invention;

FIG. 2 is a broken enlarged view of a portion of the vertebrae and spinal cord of the patient in which the neural stimulator tip and lead shown in FIG. 1 are shown in further detail in the course of installation;

FIG. 3 is a partially broken bottom plan view of a preferred embodiment of neural stimulator electrode tip incorporating the principles of the present invention;

FIG. 4 is a partially broken cross-sectioned side elevation view of the tip as viewed substantially along line 4—4 of FIG. 3; and FIG. 5 is an end view of the tip as viewed substantially along line 5—5 of FIG. 3.

DESCRIPTION OF THE PREFERRED EMBODIMENT

As shown in FIG. 1, a neural stimulator lead 10 is positioned in the epidural space of a patient's spinal column S and extends axially in that space. The lower or caudad end of the lead is electrically connected, preferably subcutaneously, to a connector conductor 12. The connector conductor 12 also preferably extends subcutaneously and, in turn, is connected to a preferably subcutaneously implanted stimulator 14 which generates electrical pulses or signals, as is known in the art, for stimulating a predetermined location on the dura of the patient's spinal cord.

The installation just described is known in the prior art. The present invention is principally directed to the construction of electrode element 16 of the lead 10 which is located at the site on the dura which is to be stimulated. As shown in the drawings, the element 16 in the preferred embodiment of the invention comprises an electrode carrying lead tip which will now be described in further detail.

In the preferred embodiment of the present invention, the tip comprises an elongate sheath 18, as best shown in FIGS. 3 and 4, having a passage 20 extending therethrough. The passage 20 is closed at the extreme distal end 22 of the tip. The passage 20 is preferably of two differing internal diameters, a smaller diameter passage 24 toward the right side of the tip as viewed in FIGS. 3 and 4 and a slightly larger diameter passage 26 toward the left side of the tip. The transition between the smaller diameter passage 24 and the larger diameter passage 26 preferably defines a step 28 against which a tubular electrode 30 is seated in the larger diameter passage 26. The electrode 30 is formed of a biologically compatible conductive metal, such as platinum.

The larger diameter passage 26, to the left of the electrode 30 as viewed in FIGS. 3 and 4, defines a coupling for receiving the sheath 32 of the lead 10 therein. The tip 16 may be firmly coupled to the exterior of the sheath 32 which extends into the larger diameter passage 26 by suitable bonding means, such as a biologically compatible adhesive.

As is typical with neural stimulator leads, the lead 10 contains a helical conductor 34 therein for conducting the stimulating current to the electrode 30. The leading end of the conductor 34 preferably extends beyond the lead sheath 32 and, when the lead sheath is installed in the tip 16, the conductor 34 extends through the electrode 30 in electrically contacting relationship thereto and into the smaller diameter passage 24, as shown in FIGS. 3 and 4. The distal end of the conductor 34 may contain a cap 36 welded thereto which is shaped to conform with the end of the passage 24, as shown in FIGS. 3 and 4. The cap 36 provides a bearing surface for the end of a stylet (not shown) which may be used for the installation of the lead and electrode element and prevents puncturing by the stylet of the distal end 22 of the tip during its placement and positioning in the patient's epidural space.

The electrode 30 communicates through the sheath 18 to the exterior thereof by way of one or more openings which pass through the sheath to the conductor. By way of example, a pair of elongate slots 38 are shown for this purpose in FIGS. 3 and 4. The slots 38 have a width which is substantially less than the perimeter of the sheath 18 of the tip. Thereby, the electrical current from the electrode is conducted from the tip in a specific direction and over only a portion of the perimeter of the tip, rather than omnidirectionally from the tip.

The electrode 30 is preferably bonded to the interior wall of the larger diameter passage 26 in the sheath by a suitable bonding material to prevent shifting of the conductor in the tip or the possibility that the conductor could fall out of the slots 38. Moreover, to prevent the latter from occurring, the electrode 30 is preferably somewhat longer than the slotted area and, thereby, extends beyond the slots 38 on one or preferably both ends of the electrode where it is entirely surrounded by the sheath. In addition, the slots 38 are preferably separated by a bridging portion 40 of the sheath adjacent the center of the electrode. The bridging portion 40 of the sheath also assists in maintaining the electrode 30 within the tip.

As previously mentioned, because the electrode 30 in the preferred embodiment shown only communicates directionally through a portion of less than the perimeter of the sheath 18 of the tip, rather than omnidirectionally through the sheath, it is particularly important in this embodiment that the slots 38 be positioned against the dura 42 of the patient, as shown in FIG. 2, and at the precise location which is to be stimulated, and that the tip and lead 10 be stabilized against rotation from that position. In the preferred embodiment of the present invention, the tip and lead are stabilized by two pairs of flexible wing members 44 and 46. The wing members 44 and 46 are preferably molded integrally with the tip sheath 18 and are thereby attached at one end to the exterior of the sheath 18 while the other ends of the wing members 44 and 46 remain free. The wing members 44 and 46 extend laterally from the sheath 18 at approximately 90° from the direction in which the slots 38 open, i.e. from the portion of the tip sheath perimeter containing the slots.

The width w of the wing members 44 and 46, as shown in FIG. 5, is substantially greater than the thickness t of the members as shown in FIG. 3. Thus, the wing members 44 and 46 are quite flexible adjacent the end to which they are attached to the sheath 18 in a direction axially of the elongate tip 16 and are readily capable of moving between their laterally extended positions at which they extend substantially 90° from the axis of the tip, as shown in solid in FIGS. 3–5, to a reclined position as shown in dot and dash. In the reclined position the wing members are positioned adjacent the exterior wall of the sheath and substantially parallel to the axis of the sheath.

Flexing to the reclined positions shown in dot and dash in FIGS. 3 and 4 facilitates insertion of the tip through a conventional hollow needle as is typically employed in the installation of epidural neural stimulators, such as a Tuohy needle 48 as shown in FIG. 2, and also facilitates passage of the tip through the epidural space 50. Once the electrode 30 and its slots 38 have been positioned at and against the desired location on the dura 42 which is to be stimulated, all that need be done is to back the lead 10 off slightly. This will cause the wing members 44 and 46 to resume their laterally extending position to stabilize the lead 10 and tip 16 against shifting and rotation. The lead and tip are stabilized against rotation due to the greater width w of the wing members 44 and 46 which results in resistance to flexing of the wing members in a direction perpendicular to the axis of the tip. The wing members also prevent lateral shifting of the lead due to their substantially greater rigidity against forces exerted along their length l as shown in FIG. 5.

It will also be seen from FIGS. 3 and 5, that the length l of the wing members 44 and 46 is less than the distance d by which the members are spaced from each other. This relationship of l to d insures that the wing members 44 and 46 are able to fully recline to their dot and dash positions, as shown in FIGS. 3 and 4, without interferring with each other during installation. By way of example, the length l of the wing members may be on the order of about twice the diameter of the sheath 18, although other wing member lengths are certainly within the principles of the invention.

It will also be seen that the ease of installation of the preferred embodiment of electrode element of the present invention is enhanced by the flexure of the wing members 44 and 46, but the tip can also be easily removed if it is found that the patient is no longer in need of neural stimulation or for replacement of the lead. As the lead 10 and tip are being withdrawn in the direction reverse to that in which they were installed, the wing members 44 and 46 will merely flex in a direction substantially parallel to the tip axis and opposite to the dot and dash positions as shown in FIGS. 3 and 4 to facilitate such withdrawal.

Although it is not absolutely necessary, it is preferred that the exterior surface of the leading end of the tip sheath 18 be of a somewhat reduced diameter to minimize the projection of the wing members 44 and 46 beyond the general perimeter outline of the tip when they are in their reclined position as shown in dot and dash in FIGS. 3 and 4. Such reduction in diameter may take the form of slight tapering of the sheath at 52 as shown in FIGS. 3 and 4.

It will be seen that in the tip of the present invention, only two stabilized rotational positions are possible, one being the position in which the slots 38 are positioned directly against the dura 42 and the other being the position in which they face away from the dura. If it is discovered during installation that the tip has been stabilized in the latter position with the slots 38 facing away from the dura, all that need generally be done is to move the lead either forward or backward along the dura to cause the wing members 44 and 46 to assume their reclined positions. Once the wing members are reclined, the lead may be rotated to rotate the slots 38 into contact with the dura. The lead 10 is then moved longitudinally to again extend the wing members 44 and 46 to their lateral positions, thus stabilizing the tip 16 in its proper position.

The sheath 18 and wing members 44 and 46, as previuosly mentioned, are preferably molded integrally with each other. They are also preferably formed of a biologically compatible material which is soft and flexible to minimize injury or pain during installation. Suitable materials may include polyurethane and Silastic.

It will be understood that various modifications may be made in the preferred embodiment just described without departing from the principles of the present invention.

For example, even though the invention has been described only in terms of the specific direction of slots 38, the sheath 18 might be removed from the electrode 30 about its full perimeter to define an omnidirectional electrode element. Although stabilization against rotation is not as important in such omnidirectional elements, the wing members 44 and 46 still effectively function to stabilize the element against lateral shifting of the element in the direction parallel to the length l of the wing members.

Although spacing of the flexible wing members 44 and 46 longitudinally of the tip and between the distal end 22 and the electrode 30 is preferred as shown, it will be understood that the wing members may also be placed at the electrode, particularly where the electrode is directional, without departing from the invention.

Moreover, although the preferred embodiment of electrode element of the invention has been described in terms of a tip for the distal end of a neural stimulator lead, the element may be positioned intermediate the length of the lead.

It will also be understood that the embodiment of the present invention which has been described is merely illustrative of one of the applications of the principles of the present invention. Numerous further modifications, in addition to those already mentioned, may be made by those skilled in the art without departing from the true spirit and scope of the invention.

What is claimed is:

1. An electrode carrying tip assembly for a neural stimulator lead of the type having an interior conductor and an exterior insulating covering, comprising:
   a tubular insulating sheath having an interior passageway for receiving one end of ht neural stimulator lead;
   a generally tubular electrode element received in said passageway having an exterior surface and including an interior bore for receiving and electrically engaging the interior conductor of the neural stimulator lead when the end of the lead is received in said passageway;

said insulating sheath having an opening through the side wall thereof adjacent said electrode element exposing a portion of said exterior surface of said electrode element to the exterior of said sheath; and stabilizing means for stabilizing said tip assembly within the spinal column of a patient including a pair of flexible elongate stabilization members extending outwardly from said sheath adjacent said opening, each of said members being attached to said sheath at one end and free at the other to allow flexure of said members from an extended position to a folded position adjacent and substantially parallel to the exterior of said sheath, hereby said tip assembly can be slidably mounted over the end of the neural stimulator lead and said stabilization members can be folded to said folded position to facilitate insertion of said tip assembly into the spinal column of a patient.

2. A tip assembly as defined in claim 1 wherein said tubular electrode element is generally cylindrical and has an exterior diameter corresponding generally to the exterior dimension of the neural stimulator lead.

3. A tip assembly as defined inc claim 2 wherein said interior bore is of generally circular cross-section and has a diameter corresponding generally to the diameter of the interior conductor of the lead.

4. A tip assembly as defined in claim 3 wherein said tubular insulating sheath is closed at one end and open at the other.

5. A tip assembly as defined in claim 4 wherein said electrode element is spaced from said closed end of said insulating sheath toward said open end.

6. A tip assembly as defined in claim 5 wherein said passageway is of generally circular cross-section and includes a region of relatively larger diameter adjacent said open end of said sheath and a region of relatively smaller diameter adjacent said closed end, said regions forming an interior step between said open and closed ends for indexing said electrode element to said position spaced from said closed end.

7. A tip assembly as defined in claim 6 wherein said larger diameter generally corresponds to the exterior diameter of said electrode element and said smaller diameter generally corresponds to the diameter of the interior conductor.

8. A tip assembly as defined in claim 7 wherein said stabilization members are mounted on said tubular insulating sheath between said opening and said closed end.

9. A tip assembly as defined in claim 8 wherein said stabilization members are mounted diameterically opposite one another on said tubular insulating sheath.

10. A tip assembly as defined in claim 9 wherein each of said stabilization members has a width which is substantially greater than its thickness, said width extending substantially perpendicular to the axis of said sheath.

11. A neural stimulator lead comprising:
an elongate electrical conductor having leading and trailing ends;
an insulating covering over said conductor having one end spaced from the tip of said leading end in a direction toward said trailing end so as to leave an uninsulated portion of said leading end of said conductor projecting beyond said one end of said covering;
a generally tubular electrode element electrically engaging a portion of said uninsulated portion of said conductor adjacent said one end of said insulating covering, said electrode element having a bore receiving said uninsulated portion of said conductor therethrough;

a generally tubular insulating sheath over said leading end of said conductor enclosing said electrode element and said one end of said covering therein, said tubular insulating sheath having a passageway therein receiving said leading end and having an aperture opening into said passageway exposing a portion of said electrode element to the exterior of said sheath; and stabilizing means for stabilizing said lead within the spiral column of a patient including a pair of elongate flexible stabilization members extending outwardly from said sheath adjacent said aperture, each of said members being attached to said sheath at one end and free at the other end to allow flexure of said members from an outwardly extending position to a folded position adjacent and substantially parallel to said exterior of said sheath.

12. A neural stimulator lead as defined in claim 11 wherein said tubular electrode element is generally cylindrical and has an exterior diameter corresponding generally to the exterior dimension of said insulating covering.

13. A neural stimulator lead as defined in claim 12 wherein said bore is of generally circular cross-section and has a diameter corresponding generally to the cross-sectional dimension of said conductor.

14. A neural stimulator lead as defined in claim 13 wherein said tubular insulating sheath is closed at one end and open at the other.

15. A neural stimulator lead as defined in claim 14 wherein said uninsulated portion of said conductor extends fully through said interior bore such that said tip of said conductor extends beyond said electrode element.

16. A neural stimulator lead as defined in claim 15 wherein said passageway is of generally circular cross-section and includes a region of relatively larger diameter adjacent said open end and a region of relatively smaller diameter adjacent said closed end, said regions forming an interior step in said passageway between said ends for indexing said electrode element to a position spaced from said closed end of said tubular sheath.

17. A neural stimulator lead as defined in claim 16 wherein said large diameter corresponds to the exterior dimension of said insulating covering and said smaller diameter corresponds to the dimension of said conductor.

18. A neural stimulator lead as defined in claim 17 wherein said stabilization members are disposed between said aperture in said tubular insulating sheath and said closed end thereof.

19. A neural stimulator lead as defined in claim 18 wherein said stabilization members are diametrically opposed on the exterior of said tubular insulating sheath.

20. A neural stimulator lead as defined in claim 19 wherein each of said stabilization members has a width which is substantially greater than its thickness, said width extending substantially perpendicular to the axis of said tubular insulating sheath.

* * * * *